United States Patent
Koizumi et al.

(10) Patent No.: US 7,156,962 B2
(45) Date of Patent: Jan. 2, 2007

(54) ELECTROLYZING ELECTRODE AND PRODUCTION METHOD THEREFOR AND ELECTROLYSIS METHOD USING ELECTROLYZING ELECTRODE AND ELECTROLYSIS SOLUTION PRODUCING DEVICE

(75) Inventors: Tomohito Koizumi, Ota (JP); Naoki Hiro, Osaka (JP); Tsuyoshi Rakuma, Ora-gun (JP); Katsuhiko Mushiake, Tokyo (JP); Masahiro Iseki, Ota (JP); Hiroyuki Umezawa, Ota (JP); Yurika Koizumi, Ora-gun (JP); Yasuhito Kondo, Ora-gun (JP)

(73) Assignee: Sanyo Electric Co., Ltd., Osaka (JP)

( * ) Notice: Subject to any disclaimer, the term of this patent is extended or adjusted under 35 U.S.C. 154(b) by 543 days.

(21) Appl. No.: 10/344,686

(22) PCT Filed: Jun. 19, 2002

(86) PCT No.: PCT/JP02/06086

§ 371 (c)(1),
(2), (4) Date: Jul. 11, 2003

(87) PCT Pub. No.: WO03/000957

PCT Pub. Date: Jan. 3, 2003

(65) Prior Publication Data
US 2004/0011665 A1 Jan. 22, 2004

(30) Foreign Application Priority Data
Jun. 21, 2001 (JP) ............... 2001-187825
Jul. 18, 2001 (JP) ............... 2001-217921
Dec. 6, 2001 (JP) ............... 2001-372589

(51) Int. Cl.
C25B 11/04 (2006.01)

(52) U.S. Cl. .......... 204/292; 204/291; 204/176; 204/252; 204/255; 204/271; 205/759; 205/760; 205/626; 205/701; 205/742; 427/126.3; 427/376.2; 502/101

(58) Field of Classification Search ......... 205/759, 205/760, 626, 701, 742; 204/176, 271, 252, 204/255, 291, 292; 502/101; 427/126.3, 427/376.2
See application file for complete search history.

(56) References Cited

U.S. PATENT DOCUMENTS

| 6,231,731 B1 * | 5/2001 | Kondo et al. .......... 204/290.03 |
| 6,736,966 B1 * | 5/2004 | Herrington et al. ......... 210/192 |
| 2003/0213704 A1 * | 11/2003 | Scheper et al. ............ 205/701 |

FOREIGN PATENT DOCUMENTS

| JP | 2-61083 | 3/1990 |
| JP | 3-271386 | 12/1991 |
| JP | 2000-160381 | 6/2000 |

* cited by examiner

Primary Examiner—Bruce F. Bell
(74) Attorney, Agent, or Firm—Armstrong, Kratz, Quintos, Hanson & Brooks, LLP

(57) ABSTRACT

There are provided an electrode for electrolysis which takes into consideration safety to human bodies and environmental pollution upon disposal of the electrode, produces ozone with high efficiency and has excellent durability, a production process of the electrode, and an active oxygen producing device using the electrode. In an electrode 5 for electrolysis which has an electrode catalyst at least on the surface and produces ozone or active oxygen in for-treatment water by electrolysis, the electrode catalyst contains a dielectric which constitutes more than 70% of the surface area of the electrode catalyst.

21 Claims, 8 Drawing Sheets

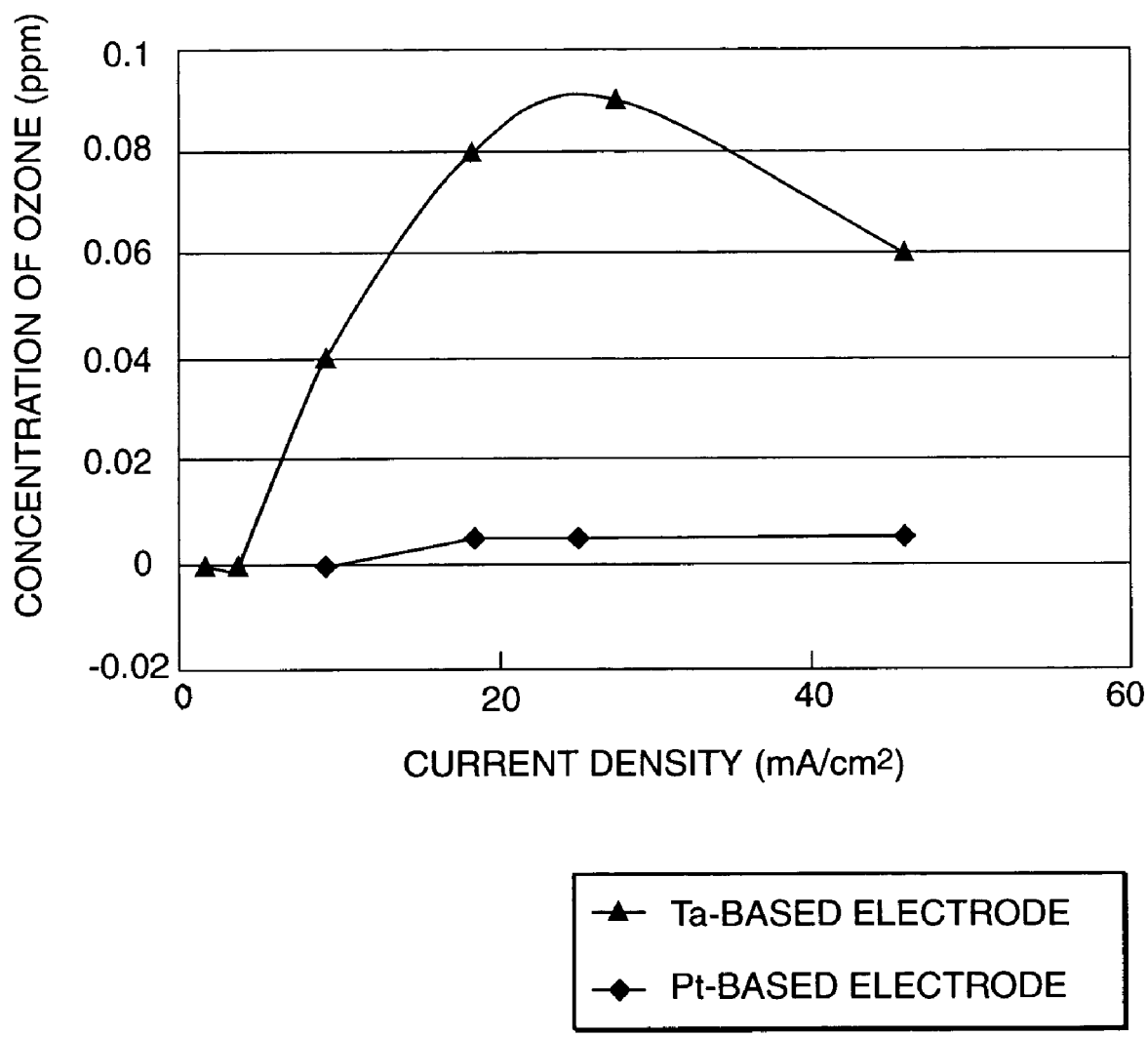

ELECTROLYZING ELECTRODE AND PRODUCTION METHOD THEREFOR AND ELECTROLYSIS METHOD USING ELECTROLYZING ELECTRODE AND ELECTROLYSIS SOLUTION PRODUCING DEVICE

BACKGROUND OF THE INVENTION

1. Field of the Invention

The present invention is aimed at cleansing a variety of bacteria and contaminants and relates to an electrode for electrolysis which is capable of producing ozone and active oxygen with high efficiency, a production process of the electrode, an electrolytic process using the electrode, and an electrolyzed water producing device using the electrode.

2. Description of the Related Art

Heretofore, to remove microorganisms such as bacteria, fungi and protozoans contained in domestic water for drinking and cooking and water (hereinafter referred to as "for-treatment water") used in a kitchen or other places, a method in which the for-treatment water is sterilized and purified by use of a chlorine-based agent such as sodium hypochlorite has been used. However, the for-treatment water contains chlorine-resistant bacteria, spores and protozoans, and they are difficult to remove by use of only hypochlorous acid. Hence, a method in which the for-treatment water is sterilized and purified by use of ozone is used.

As means for producing the ozone, it is generally practiced to use, as an anode, an electrode for electrolysis which comprises a titanium substrate whose surface is coated with a lead oxide or a tin oxide. The electrode coated with the lead oxide or tin oxide is capable of producing ozone and active oxygen with high efficiency. Therefore, the electrode can be considered particularly effective when the fore-treatment water is treated with high concentrations of ozone and active oxygen.

However, since the lead oxide is designated as a toxic substance by water quality regulations as a lead compound, the electrode coated with the lead oxide has a problem that when water treated with the electrode is taken in a human body, the water causes a variety of troubles in the human body. Meanwhile, the electrode coated with the tin oxide has a problem in terms of durability since the tin oxide is liable to be eluted by electrolysis. Thus, there has been a problem that it is difficult to carry out electrolysis of for-treatment water by use of an electrode for electrolysis which has a substrate coated with the lead oxide or tin oxide.

Under the circumstances, to avoid the above problems, a method has been used in which ozone is produced by use of an electrode for electrolysis which has a substrate coated with a noble metal such as platinum or a metal oxide. However, the method has a problem that with the electrode, the efficiency of production of ozone is significantly lower than that with an electrode coated with a lead oxide.

Accordingly, the amount of ozone dissolved in for-treatment water is small, so that the sterilizing effect of ozone is not so favorable.

Meanwhile, a problem of infectious diseases caused by bacteria such as Legionella bacteria which grow in a bathroom in particular has recently been receiving attention. At humidities and temperatures in a bathroom, growth of fungi and proliferation of bacteria such as Legionella bacteria are spurred, and when these fungi and Legionella bacteria enter a human body, they cause infectious diseases in the human body. In general, fungi and Legionella bacteria which have proliferated in an environment with high humidity and temperature such as a bathroom are deposited on a bathtub and tiles and diffused into hot water reserved in the bathtub. When one inhales steam generated from the hot water, the bacteria enter his body.

Further, in addition to the bathtub, in sinks as in a kitchen, when small pieces of food or water are rotten, they cause proliferation of bacteria.

In addition, the foregoing bacteria such as Legionella bacteria are also stuck to an air conditioner, air cleaner, ventilating fan, and the like, and upon operation of these apparatuses, the bacteria are discharged into a room from an air outlet and float in the air. There is a problem that these floating bacteria cause infectious diseases.

Under the circumstances, a chlorine-based bactericide is generally applied to a bathtub, tiles, kitchen sink and air outlet as of air conditioning equipment where bacteria such as fungi and Legionella bacteria are deposited, so as not only to kill the bacteria such as fungi but also to prevent further proliferation of the bacteria.

Most of generally used chlorine-based bactericides are adjusted to be alkaline by incorporation of agents such as sodium hypochlorite. Further, the chlorine-based bactericide has a problem that it generates a chlorine gas when mixed with an acidic agent, thereby causing an accident during use. In addition, the chlorine-based bactericide also has a problem that it has difficulty in eliminating chlorine-resistant bacteria, spores and protozoans.

Further, as another sterilization method, a sterilization method using silver ions as bactericidal metal ions is known. The sterilization method based on the silver ions comprises the steps of reserving service water as for-electrolysis water in a vessel, electrolyzing the service water by means of silver electrodes immersed in the service water so as to generate silver ions in the service water, and spraying the service water containing the silver ions for the purpose of sterilization.

However, the above method has a problem that since the silver electrodes are eluted by the electrolysis, the electrodes become unable to be used as electrodes due to the elution of the electrodes even if polarities of the electrodes are switched, thereby decreasing a sterilizing effect. Further, the method also has a problem that since a relatively expensive noble metal is used in the electrodes, costs increase steeply when the electrodes are used over a long time period.

With this being the situation, as still another sterilization method, there is a method comprising the steps of producing electrolyzed water containing a high concentration of hypochlorous acid through electrolysis using electrodes and carrying out sterilization by use of the electrolyzed water. However, the method has the following problem. That is, when the electrolyzed water containing hypochlorous acid is used, salts remain where the solution has been applied, so that when the electrolyzed water is used for sterilizing hands and fingers, the hands and fingers must be rinsed after the sterilization.

The present invention has been conceived so as to solve the technical problems of the prior art. An object of the present invention is to propose an electrode for electrolysis which takes into consideration safety to human bodies and environmental pollution upon disposal of the electrode, produces ozone with high efficiency and has excellent durability, a production process of the electrode, and an electrolytic process for producing ozone or active oxygen.

Further, another object of the present invention is to provide an electrolyzed water producing device which can achieve sterilization by using electrolyzed water which exhibits a high sterilizing effect without using a chlorine-based agent.

SUMMARY OF THE INVENTION

An electrode for electrolysis of the present invention is an electrode which has an electrode catalyst at least on a surface thereof and produces ozone or active oxygen in for-treatment water by electrolysis, wherein the electrode catalyst contains a dielectric, which occupies more than 70% of the surface area of the electrode catalyst.

Further, in the electrode of the present invention, a noble metal or metal oxide is present in a surface portion of the electrode catalyst which is not constituted by the dielectric.

Further, an electrode for electrolysis of the present invention is an electrode which has an electrode catalyst surface layer formed on the surface of a conductive substrate and produces ozone or active oxygen in for-treatment water by electrolysis, wherein the electrode catalyst surface layer contains a dielectric in an amount of more than 70 mol %.

Further, in the electrode of the present invention, the electrode catalyst surface layer contains a noble metal or metal oxide.

Further, in the electrode of the present invention, the electrode catalyst surface layer contains at least a tantalum oxide in an amount of 70 mol % as the dielectric and contains at least platinum as the noble metal or metal oxide, or the electrode catalyst surface layer contains at least a niobium oxide in an amount of 70 mol % as the dielectric and contains at least a ruthenium oxide as the noble metal or metal oxide.

A process for producing the electrode of the present invention is a process which comprises the steps of:
coating the surface of the conductive substrate with a surface layer forming material containing a tantalum oxide, a tantalum oxide precursor, a niobium oxide or a niobium oxide precursor, and
heat-treating the conductive substrate and the surface layer forming material in an oxidizing atmosphere.

Further, in the production process of the present invention, the conductive substrate which is tantalum, a tantalum alloy, niobium or a niobium alloy is oxidized to form the electrode catalyst surface layer.

Further, in an electrolytic process of the present invention for producing ozone or active oxygen, an anode and a cathode are immersed in for-treatment water in an electrolysis vessel, and the foregoing electrode is used as the anode.

Further, in the electrolytic process of the present invention, the anode and the cathode are separated from each other by a cation exchange membrane.

Further, in an electrolytic process of the present invention for producing ozone or active oxygen, an anode and a cathode are immersed in for-treatment water in an electrolysis vessel, the foregoing electrode is used as the anode and the cathode, and a pulse voltage is applied to between the anode and the cathode in the for-treatment water.

Further, an electrolyzed water producing device of the present invention is a device which has a portable applicator comprising:
a reservoir for reserving water to be electrolyzed,
a pair or plurality of electrodes for electrolysis which are provided in the reservoir so as to be immersed in the for-electrolysis water, and
an outlet for discharging the liquid out of the reservoir, and
which passes an electric current in between the electrodes so as to produce ozone or active oxygen in the for-electrolysis water.

Further, in the device of the present invention, the electrode has an electrode catalyst at least on the surface, the electrode catalyst contains a dielectric, and the dielectric constitutes more than 70% of the surface area of the electrode catalyst.

Further, in the device of the present invention, a noble metal or metal oxide is present in a surface portion of the electrode catalyst which is not constituted by the dielectric.

Further, in the device of the present invention, the electrode has an electrode catalyst surface layer formed on the surface of a conductive substrate, and the electrode catalyst surface layer contains a dielectric in an amount of more than 70 mol %.

Further, in the device of the present invention, the electrode catalyst surface layer contains at least a tantalum oxide in an amount of 70 mol % as the dielectric and contains at least platinum as the noble metal or metal oxide, or the electrode catalyst surface layer contains at least a niobium oxide in an amount of 70 mol % as the dielectric and contains at least a ruthenium oxide as the noble metal or metal oxide.

Further, in the device of the present invention, the electrode comprises titanium coated with a mixture of platinum as the noble metal or metal oxide and a tantalum oxide as the dielectric.

Further, in the device of the present invention, a power supply for energizing the electrodes in the applicator from outside the applicator is provided independently of the applicator.

Further, in the device of the present invention, the applicator incorporates a power supply for energizing the electrodes.

Further, in the device of the present invention, a controller for controlling energization of the electrodes is provided, and the controller is capable of changing the concentration of electrolyzed water produced in the reservoir.

Further, in the device of the present invention, the controller is provided in the power supply.

Further, in the device of the present invention, the controller switches polarities of the electrodes from one polarity to the other polarity.

Further, in the device of the present invention, the applicator has an operating part, and based on operation of the operating part, the electrolyzed water produced in the reservoir is pushed toward the outlet so as to be sprayed out therefrom.

BRIEF DESCRIPTION OF THE DRAWINGS

FIG. 9 is a diagram showing a relationship between concentrations of ozone produced by electrodes for electrolysis of the electrolyzed water producing device and current densities.

DETAILED DESCRIPTION OF THE PREFERRED EMBODIMENT

Figure 1:
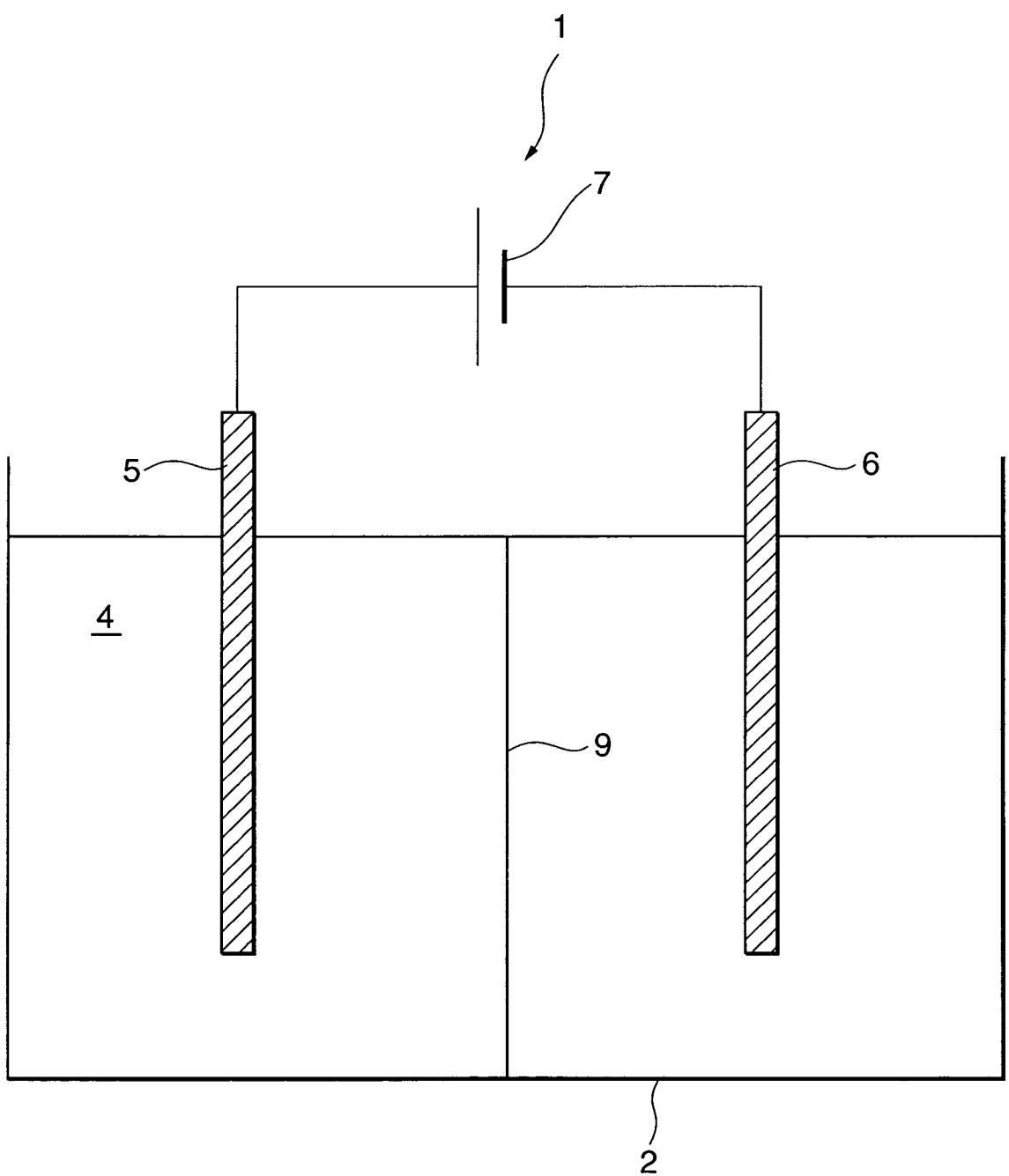
FIG. 1 is a schematic block diagram of an ozone or active oxygen producing device for illustrating the present invention.

Hereinafter, embodiments of the present invention will be described in detail with reference to the drawings. FIG. 1 is an explanatory diagram showing an overview of an ozone or active oxygen producing device 1 which adopts an electrode for electrolysis of the present invention. The ozone or active oxygen producing device 1 in the present embodiment comprises an electrolysis vessel 2 which constitutes a treating chamber 4 having an inlet and an outlet for-treatment water which are not shown in the chamber, a pair of electrodes for electrolysis which are disposed so as to confront each other with at least portions of the electrodes immersed in for-treatment water in the treating chamber 4, i.e., an electrode 5 for electrolysis which serves as an anode and an electrode 6 for electrolysis which serves as a cathode, and a power supply 7 for energizing the electrodes 5 and 6.

It is to be noted that in the drawing, a member 9 interposed between the electrode 5 which serves as the anode and the electrode 6 which serves as the cathode in the electrolysis vessel 2 is a cation exchange membrane.

The electrode 5 which serves as an anode comprises a conductive substrate composed of a conductive material such as titanium and an electrode catalyst formed at least on the surface of the conductive substrate. The electrode catalyst is a catalyst formed as a surface layer of the conductive substrate and immersed in for-treatment water so as to contribute to electrolysis directly. In the present invention, an electrode for electrolysis is an electrode that is immersed in for-treatment water so as to contribute to electrolysis directly and includes portions which constitute the electrode and directly contribute to electrolysis.

On the surface of a portion of the conductive substrate which is to be immersed in for-treatment water, a surface layer forming material which serves as the electrode catalyst is applied. The surface layer forming material contains a dielectric in an amount of more than 70 mol %. In the present embodiment, the surface layer forming material comprises 90 mol % of tantalum oxide ($Ta_2O_5$) as the dielectric and a noble metal or metal oxide. In the present embodiment, the surface layer forming material comprises 10 mol % of platinum (Pt) as the noble metal or metal oxide.

Then, after the surface layer forming material is dried, the substrate coated with the surface layer forming material is heat-treated at temperatures of +300 to +700° C. in an oxidizing atmosphere. Thereby, on the surface portion of the substrate which directly contributes to electrolysis, that is, the electrode catalyst portion, an electrode catalyst surface layer comprising the tantalum oxide and platinum is formed.

As a result, adhesion between the surface layer forming material and the substrate is improved, and a dense electrode catalyst surface layer can be formed.

The surface layer forming material may be applied by a method in which the substrate is immersed in a container containing the tantalum oxide and platinum or a method in which the surface layer forming material is applied by use of a brush or an equivalent tool. The application and heat treatment of the surface layer forming material may be repeated for a plurality of times, e.g., 20 times, to form the electrode catalyst surface layer, only the outermost surface may be formed by the surface layer forming material containing the dielectric in an amount of more than 70 mol%.

Meanwhile, the electrode 6 which serves as a cathode may have the same constitution as that of the electrode 5 which serves as an anode. Alternatively, the electrode 6 may be composed of an insoluble material or carbon.

With the above constitution, for-treatment water is reserved in the treating chamber 4 in the electrolysis vessel 2, and the power supply 7 is turned on so as to energize the electrode 5 which serves as an anode and the electrode 6 which serves as a cathode. As a result, microorganisms such as bacteria, fungi and protozoans in the for-treatment water which are generally negatively charged are attracted to the positively charged electrode 5 which serves as an anode.

The electrode 5 which serves as an anode is immersed in the for-treatment water. Since the electrode catalyst surface layer which directly contributes to electrolysis contains at least a tantalum oxide as a dielectric and platinum as a noble metal or metal oxide, the tantalum oxide and platinum serve as catalysts in the electrolysis. Thereby, production of oxygen is suppressed, so that efficiency of production of ozone or active oxygen can be improved.

Further, in the present embodiment, since the electrode catalyst surface layer contains the tantalum oxide as a dielectric in an amount of more than 70 mol %, catalytic action in the electrolysis is invigorated, the production of oxygen is suppressed, and the efficiency of production of ozone or active oxygen can be further improved.

In particular, since the electrode having the electrode catalyst surface layer formed thereon is used as the electrode 5 which serves as an anode, active oxygen radicals and hydroxy radicals can also be produced.

Thus, the microorganisms such as bacteria, fungi and protozoans which have been attracted to the electrode 5 which serves as an anode can be killed effectively by produced ozone, active oxygen radicals and hydroxy radicals.

Further, since a portion of the electrode catalyst surface layer which is not constituted by the tantalum oxide is constituted by a noble metal or metal oxide such as platinum, the conductivity of the electrode is increased by platinum, so that the efficiency of the electrolysis can be improved.

Further, in the present embodiment, a mixture of a tantalum oxide and a noble metal or metal oxide is used as the surface layer forming material to be applied on the surface of the conductive substrate. However, the same effect as described above can still be achieved with a mixture of a tantalum oxide precursor and a noble metal or metal oxide.

The electrode in the present embodiment is constituted by the surface layer forming material comprising more than 70 mol % of dielectric, i.e., 90 mol % of tantalum oxide, and 10 mol % of platinum as a noble metal or metal oxide. In addition to this, the electrode may also be constituted such that the dielectric constitutes more than 70% of the surface area of the electrode catalyst portion of the electrode after the electrode catalyst surface layer is formed by the surface layer forming material, that is, the portion which is immersed in for-treatment water so as to directly contribute to electrolysis.

Further, in the electrode catalyst portion of the electrode, a noble metal or a metal oxide exists in a surface portion of the electrode catalyst which is not constituted by the tantalum oxide which is a dielectric.

This also causes the conductivity of the electrode to improve, whereby the efficiency of the electrolysis can be improved.

Furthermore, in the above embodiment, the conductive substrate of the electrode comprises titanium. Alternatively, the conductive substrate may comprise tantalum or a tantalum alloy and be oxidized to form the electrode catalyst surface layer.

The conductive substrate is oxidized by a method comprising the steps of immersing the conductive substrate in, for example, a sulfuric acid solution and energizing the conductive substrate so as to form an oxide film, i.e., the electrode catalyst surface layer, on the surface of the conductive substrate.

Thereby, the electrode for electrolysis can be formed without using relatively expensive noble metals, thereby reducing costs. In addition, since the electrode catalyst surface layer can be formed only by oxidizing the conductive substrate, a production process can be simplified.

Further, in the present embodiment, in the electrolysis vessel 2, the cation exchange membrane 9 is interposed between the electrode 5 which serves as an anode and the electrode 6 which serves as a cathode. This can cause hydrogen ions produced by electrolysis to move from the electrode 5 which serves as an anode toward the electrode 6 which serves as a cathode so as to accelerate production of hydrogen at the electrode 6 which serves as a cathode. Thereby, a potential can be increased, and along with the increase in the potential, the amount of production of ozone can also be increased.

Meanwhile, as another electrolytic process using the foregoing electrode for electrolysis, there is a process in which the electrode constituted as described above is used as the electrode 5 which serves as an anode and the electrode 6 which serves as a cathode, the electrode 5 which serves as an anode and the electrode 6 which serves as a cathode are immersed in for-treatment water in the electrolysis vessel 2, and a pulse voltage is applied to between the electrode 5 which serves as an anode and the electrode 6 which serves as a cathode.

Generally, hydroxy radicals are vigorously produced by the electrode 5 which serves as an anode at the moment when a voltage is applied to between the electrode 5 which serves as an anode and the electrode 6 which serves as a cathode. Accordingly, application of a pulse voltage to between the electrode 5 which serves as an anode and the electrode 6 which serves as a cathode can cause efficient production of the hydroxy radicals.

Figure 2:
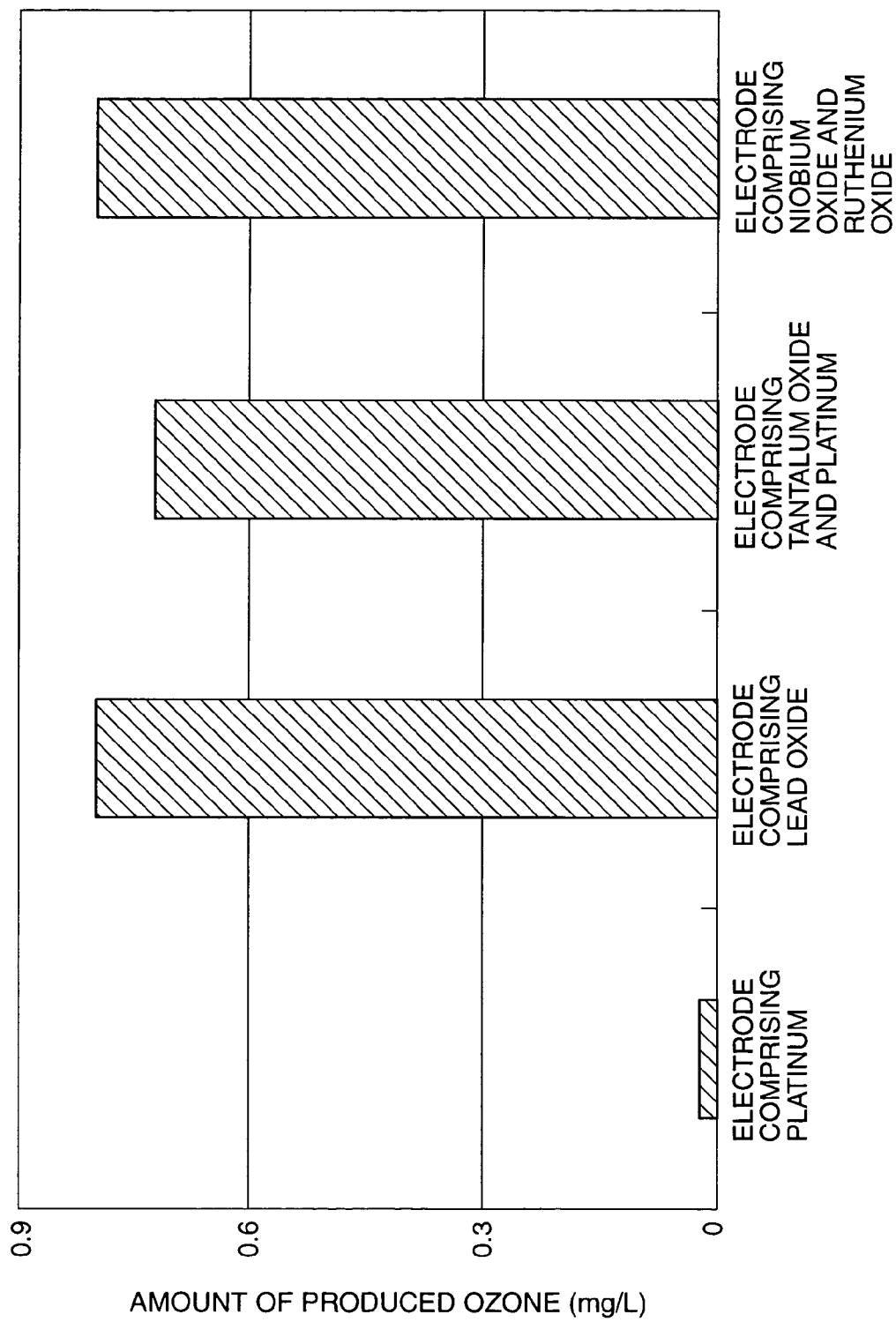
FIG. 2 is a diagram showing amounts of ozone produced at various types of electrodes.

Next, the electrode for electrolysis according to the present invention will be described in comparison with other electrodes for electrolysis. FIG. 2 shows amounts of ozone produced in a phosphate buffer electrolytic solution. FIG. 2 shows, from the left to the right, amounts of ozone produced by a platinum electrode, a lead oxide electrode, the electrode comprising a tantalum oxide and platinum according to the present invention, and an electrode comprising a niobium oxide and a ruthenium oxide. The platinum electrode is an electrode for electrolysis which has heretofore been used in an ozone producing device and comprises a conductive material coated with platinum as a noble metal. The lead oxide electrode is an electrode for electrolysis which is used in an ozone producing device for sterilizing for-treatment water having a significantly low possibility of influencing human bodies and comprises a conductive material coated with a lead oxide.

FIG. 2 shows the results of measurements of amounts of ozone produced when electrolysis of for-treatment water was carried out by using each of the above electrodes as the electrode 5 which serves as an anode under the same conditions. Referring to FIG. 2, the amount of ozone produced with the platinum electrode is 0.015 mg/L, the amount of ozone produced with the lead oxide electrode is 0.80 mg/L, the amount of ozone produced with the electrode according to the present invention which comprises a tantalum oxide and platinum as electrode catalysts is 0.72 mg/L, and the amount of ozone produced with the electrode comprising a niobium oxide and a ruthenium oxide as electrode catalysts is 0.80 mg/L. In the electrode of the present invention which has the electrode catalyst surface layer comprising the tantalum oxide and platinum, the tantalum oxide constitutes at least 90 mol % of the electrode catalyst surface layer. In the electrode having an electrode catalyst surface layer comprising the niobium oxide and the ruthenium oxide, the niobium oxide constitutes at least 90 mol % of the electrode catalyst surface layer.

It is understood from FIG. 2 that the amount of ozone produced when electrolysis of for-treatment water is carried out by use of the electrode of the present invention is about 50 times as much as that when electrolysis is carried out by use of the platinum electrode.

Further, it is also understood that the amount of ozone produced when electrolysis is carried out by use of the electrode of the present invention is about the same as that when electrolysis is carried out by use of the lead oxide electrode.

Thus, since the electrode having the electrode catalyst surface layer comprising the tantalum oxide and platinum and the electrode having the electrode catalyst surface layer comprising the niobium oxide and the ruthenium oxide have significantly higher ozone production efficiency than the conventionally used electrode coated with a noble metal such as platinum, an effect of sterilizing for-treatment water by ozone can be improved. Accordingly, while additives and a special device are required to improve the ozone production efficiency when the platinum electrode is used, ozone concentration suitable for practical use can be attained without relying on such special means.

Consequently, costs of the ozone or active oxygen producing device 1 can be reduced, and productivity and ease of maintenance thereof can be improved.

Further, since the electrode of the present invention is free from a lead compound designated as a toxic substance by water quality regulations and produced when a lead oxide electrode is used, it can sterilize for-treatment water safely without causing any troubles on human bodies. Therefore, sterilized and purified for-treatment water can be directly used for drinking or sterilization of cooking utensils. Further, upon disposal of the electrode, it does not produce a lead compound, so that the electrode can sufficiently contribute to prevention of environmental pollution.

Figure 3:
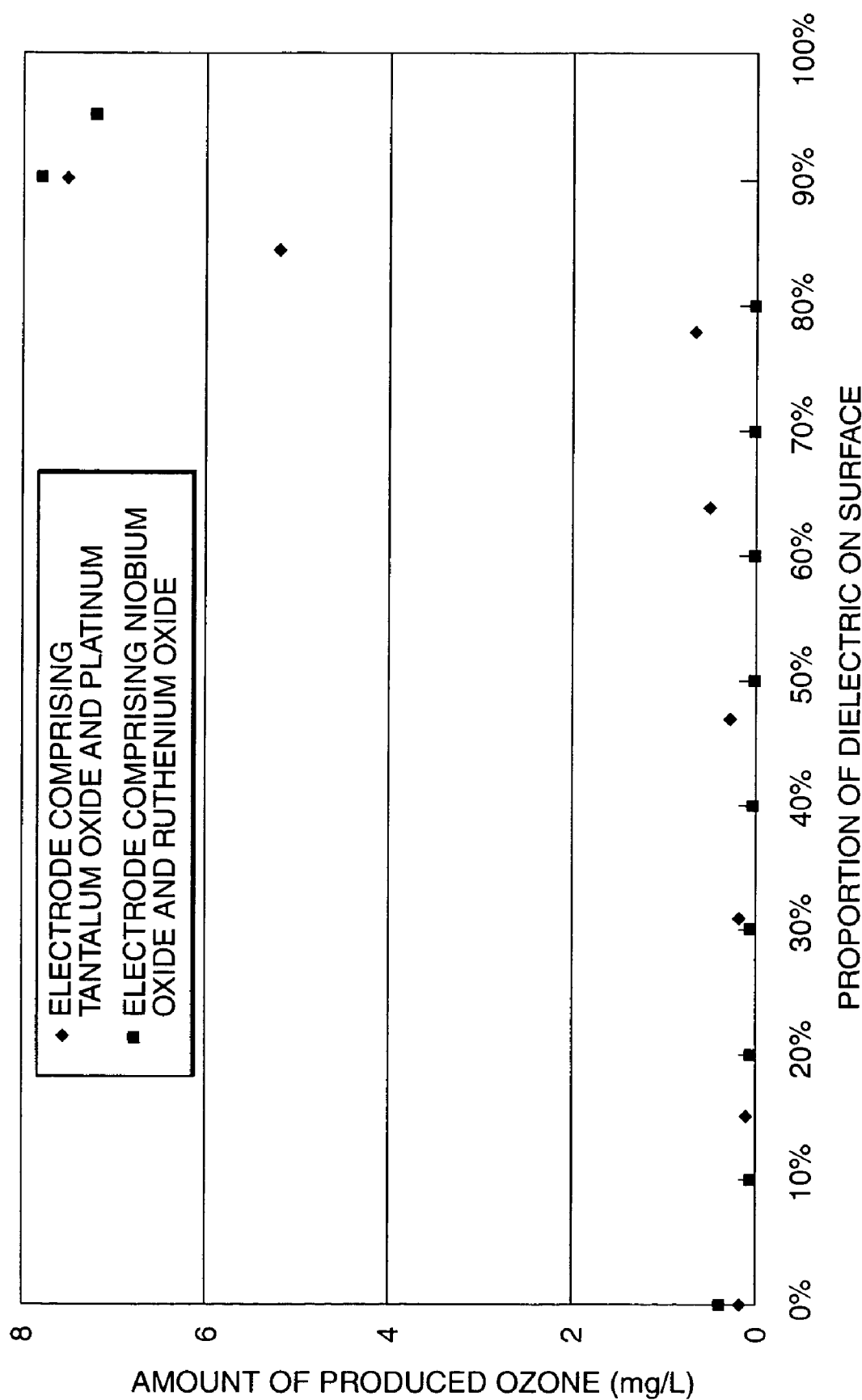
FIG. 3 is a diagram showing amounts of ozone produced at an electrode containing a tantalum oxide as a dielectric and an electrode containing a niobium oxide as a dielectric with proportions of the dielectrics on the surfaces of the electrodes varied.

Next, a relationship between the amount of production of ozone and the proportion of the tantalum oxide on the surface of the electrode according to the present invention and a relationship between the amount of production of ozone and the proportion of a niobium oxide on the surface of an electrode comprising the niobium oxide will be described with reference to FIG. 3. FIG. 3 shows amounts of ozone produced with the electrodes according to the present invention which have different proportions of the tantalum oxide on their surfaces and amounts of ozone produced with the electrodes having different proportions of the niobium oxide on their surfaces, using service water as for-treatment water.

Under the same conditions, the amount of ozone produced when service water was electrolyzed by use of each of these electrodes was measured. In the experiment, electrolysis was carried out by use of an electrode with a proportion of the tantalum oxide on the surface of 15% (hereinafter referred to as "Ta-15% electrode"), an electrode with a proportion of the tantalum oxide on the surface of 31% (hereinafter referred to as "Ta-31% electrode"), an electrode with a proportion of the tantalum oxide on the surface of 47% (hereinafter referred to as "Ta-47% electrode"), an electrode with a proportion of the tantalum oxide on the surface of 64% (hereinafter referred to as "Ta-64% electrode"), an electrode with a proportion of the tantalum oxide on the surface of 78% (hereinafter referred to as "Ta-78% electrode"), an electrode with a proportion of the tantalum oxide on the surface of 84% (hereinafter referred to as "Ta-84% electrode"), and an electrode with a proportion of the tantalum oxide on the surface of 90% (hereinafter referred to as "Ta-90% electrode"). In addition, electrolysis was carried out by use of an electrode with a proportion of the niobium oxide on the surface of 10% (hereinafter referred to as "Nb-10% electrode"), an electrode with a proportion of the niobium oxide on the surface of 20% (hereinafter referred to as "Nb-20% electrode"), an electrode with a proportion of the niobium oxide on the surface of 30% (hereinafter referred to as "Nb-30% electrode"), an electrode with a proportion of the niobium oxide on the surface of 40% (hereinafter referred to as "Nb-40% electrode"), an electrode with a proportion of the niobium oxide on the surface of 50% (hereinafter referred to as "Nb-50% electrode"), an electrode with a proportion of the niobium oxide on the surface of 60% (hereinafter referred to as "Nb-70% electrode"), an electrode with a proportion of the niobium oxide on the surface of 80% (hereinafter referred to as "Nb-80% electrode"), an electrode with a proportion of the niobium oxide on the surface of 90% (hereinafter referred to as "Nb-90% electrode"), and an electrode with a proportion of the niobium oxide on the surface of 95% (hereinafter referred to as "Nb-95% electrode").

The results of the experiment are as follows. With the Ta-15% electrode, 0.1 mg/L of ozone was produced; with the Ta-31% electrode, 0.16 mg/L of ozone was produced; with the Ta-47% electrode, 0.28 mg/L of ozone was produced; with the Ta-64% electrode, 0.5 mg/L of ozone was produced; with the Ta-78% electrode, 0.66 mg/L of ozone was produced; with the Ta-84% electrode, 5.2 mg/L of ozone was produced; and with the Ta-90% electrode, 7.5 mg/L of ozone was produced. Meanwhile, with the Nb-10% to Nb-80% electrodes, 0.1 mg/L of ozone was produced; with the Nb-90% electrode, 7.8 mg/L of ozone was produced; and with the Nb-95% electrode, 7.2 mg/L of ozone was produced.

According to these results of the experiment, it is understood that the amount of produced ozone sharply increases when the proportion of the tantalum oxide or niobium oxide as a dielectric on the surface is 80% or higher. For this reason, the electrode according to the present invention may be one having an electrode catalyst surface layer formed by use of a surface layer forming material which achieves a proportion of the tantalum oxide or niobium oxide as a dielectric on the surface of not lower than 80%. Thereby, the amount of production of ozone can be further increased.

In general, the tantalum oxide or niobium oxide which is a dielectric is used in an electrode for electrolysis for the purpose of improving adhesion between pits and projections occurring between a conductive substrate and a coating noble metal or metal oxide as well as durability of the electrode. It is understood that when the amount of such a tantalum oxide or niobium oxide as a dielectric which is used to improve the adhesion and durability is significantly increased, the amount of production of ozone can be sharply increased.

It is assumed that this is because the tantalum oxide or niobium oxide as a dielectric acts in the surface layer of the electrode for electrolysis so as to produce ozone.

Further, when a noble metal or metal oxide is used in a portion of the surface layer which is not occupied by the tantalum oxide or niobium oxide as a dielectric, catalytic action is invigorated, conductivity can be further improved, and efficiency of production of ozone can be improved.

According to the foregoing constitution, when for-treatment water is electrolyzed by use of the electrode according to the present invention, ozone or active oxygen can be produced without significantly increasing an electric current value. Consequently, microorganisms, chlorine-resistant bacteria, spores and protozoans contained in the for-treatment water can be killed with ease by ozone having very strong bactericidal activity.

Next, an embodiment of an electrolyzed water producing device using the electrode for electrolysis of the present invention will be described hereinafter.

Figure 4:
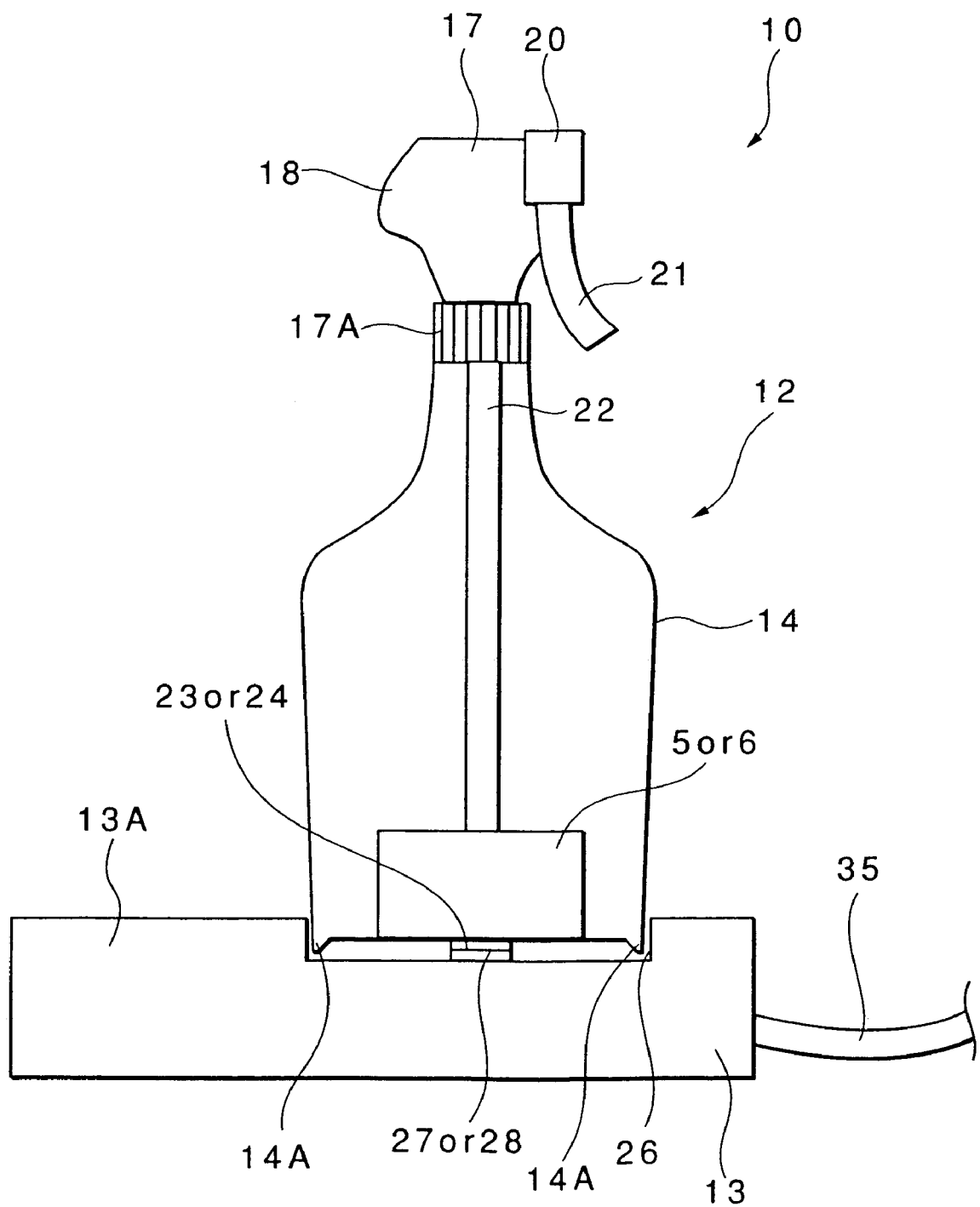
FIG. 4 is a diagram for illustrating an overview of an electrolyzed water producing device of the present invention.
Figure 5:
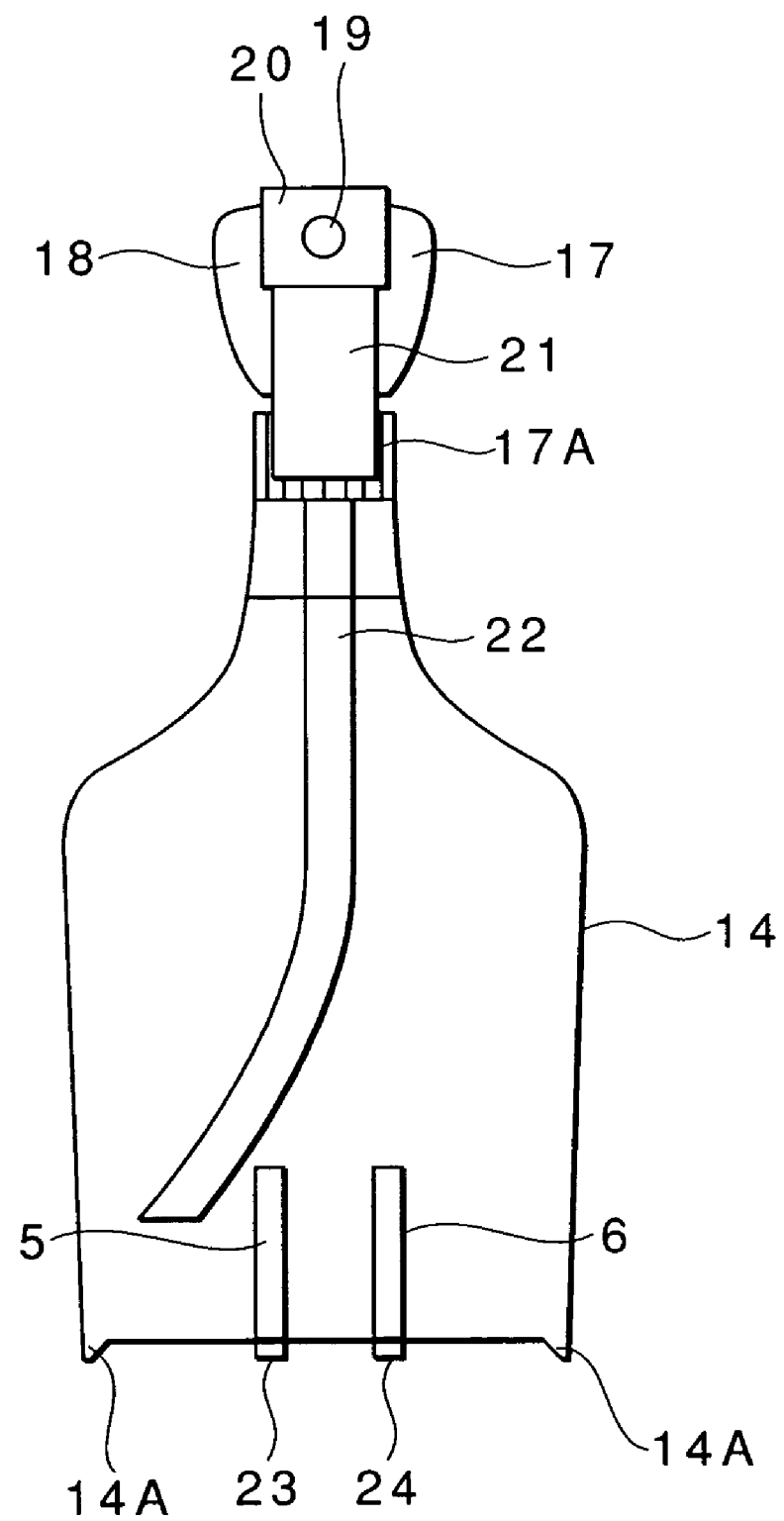
FIG. 5 is a front view of an applicator of the electrolyzed water producing device.
Figure 6:
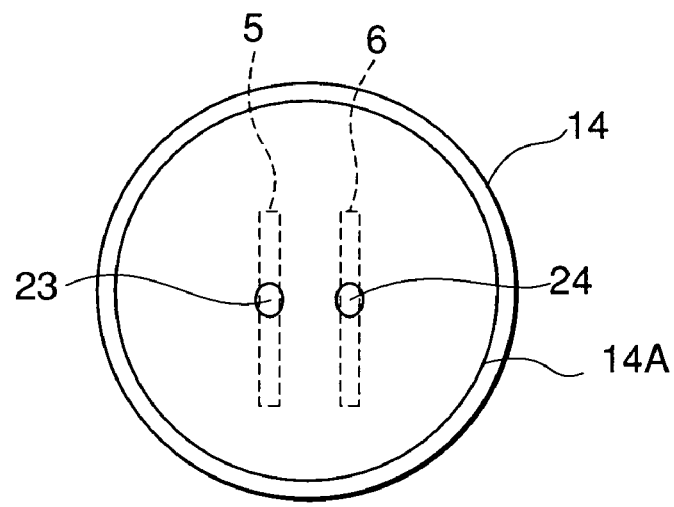
FIG. 6 is a bottom view of the applicator of the electrolyzed water producing device.

FIG. 4 is an explanatory diagram showing an overview of an electrolyzed water producing device 10 of an embodiment of the present invention. FIG. 5 is a front view of an applicator 12. FIG. 6 is a bottom view of the applicator 12. The electrolyzed water producing device 10 in the present embodiment comprises the portable applicator 12 and a power supply 13.

The applicator 12 comprises a reservoir 14 for reserving water to be electrolyzed (which is generally service water) which is for-treatment water in this case, the aforementioned electrodes 5 and 6 for electrolysis, and a discharge portion 17 for discharging electrolyzed water (sterilized water) produced in the reservoir 14 out of the applicator 12. The reservoir 14 is a vessel having an inlet for-electrolysis water (service water) formed on the top, for example. Around the inlet is formed a screw groove in which a cap 17A as a cap member which is attached to the discharge portion 17 is screwed so as to detachably secure the cap 17A. The screw grove is not shown.

The cap 17A has a so-called vent hole or pressure value for exhausting gas from the reservoir 14. The hole or valve is also not shown.

Further, the reservoir 14 has a volume of, for example, about 500 ml so that it can still be easily carried even when containing for-electrolysis water. In addition, the bottom of the reservoir 14, as shown in FIGS. 5 and 6, has a slightly downwardly protruding outer edge 14A so that the bottom of the reservoir 14 inside the edge 14A is a predetermined distance away from a surface with which the edge 14A makes contact.

The discharge portion 17 is a so-called spray-type discharge member and comprises a main body 18 on which the cap 17A is attached, a discharge member 20 which has an outlet 19 formed on the front of the main body 18, an operating part 21 which is attached to the discharge member 20 and operated to discharge sterilized water, and a supply pipe 22 which extends downwardly inside the reservoir 14 and is immersed in for-electrolysis water (or electrolyzed water after electrolysis) in the reservoir 14.

Thus, through operation of the operating part 21 of the discharge portion 17, via the supply pipe 22 immersed in the for-electrolysis water (or electrolyzed water), the for-electrolysis water (or electrolyzed water) can be sprayed out from the outlet 19.

Meanwhile, the electrodes 5 and 6 are disposed at the bottom inside the reservoir 14. In this case, the electrodes 5 and 6 each comprise a flat conductive substrate comprising titanium (or a titanium alloy) which is a conductive material and an electrode catalyst formed at least on the surface of the conductive substrate. The electrode catalyst, as described above, is a catalyst which is formed as a surface layer of the conductive substrate and is immersed in for-electrolysis water and directly contributes to electrolysis. Further, in this case as well, the electrode for electrolysis is an electrode that is immersed in for-electrolysis water and directly contributes to electrolysis and includes a portion of the electrode which is immersed in for-electrolysis water and directly-contributes to electrolysis.

Further, in this case as well, a surface layer forming material is applied on the surface of the conductive substrate so as to form the electrode catalyst. Further, in this case as well, the surface layer forming material contains a dielectric in an amount of more than 70 mol %. In the present embodiment, the surface layer forming material comprises 90 mol % of tantalum oxide ($Ta_2O_5$) as the dielectric and a noble metal or metal oxide. In the present embodiment, the surface layer forming material comprises 10 mol % of platinum (Pt) as the noble metal or metal oxide.

In the present embodiment, although only a pair of electrodes 5 and 6 are disposed at the bottom inside the reservoir 4, more electrodes (3 or more electrodes) for electrolysis may be provided.

Further, in this case, the electrodes 5 and 6 have terminals 23 and 24, respectively. These terminals 23 and 24 are exposed to the central portion of the outer bottom surface of the reservoir 14 via holes formed at the bottom of the reservoir 14. The holes are not shown. The terminals 23 and 24 are positioned at a position higher than the lower end of the outer edge 14A of the reservoir 14. Thus, one can place the applicator 12 on a flat surface such as a table safely.

Figure 7:
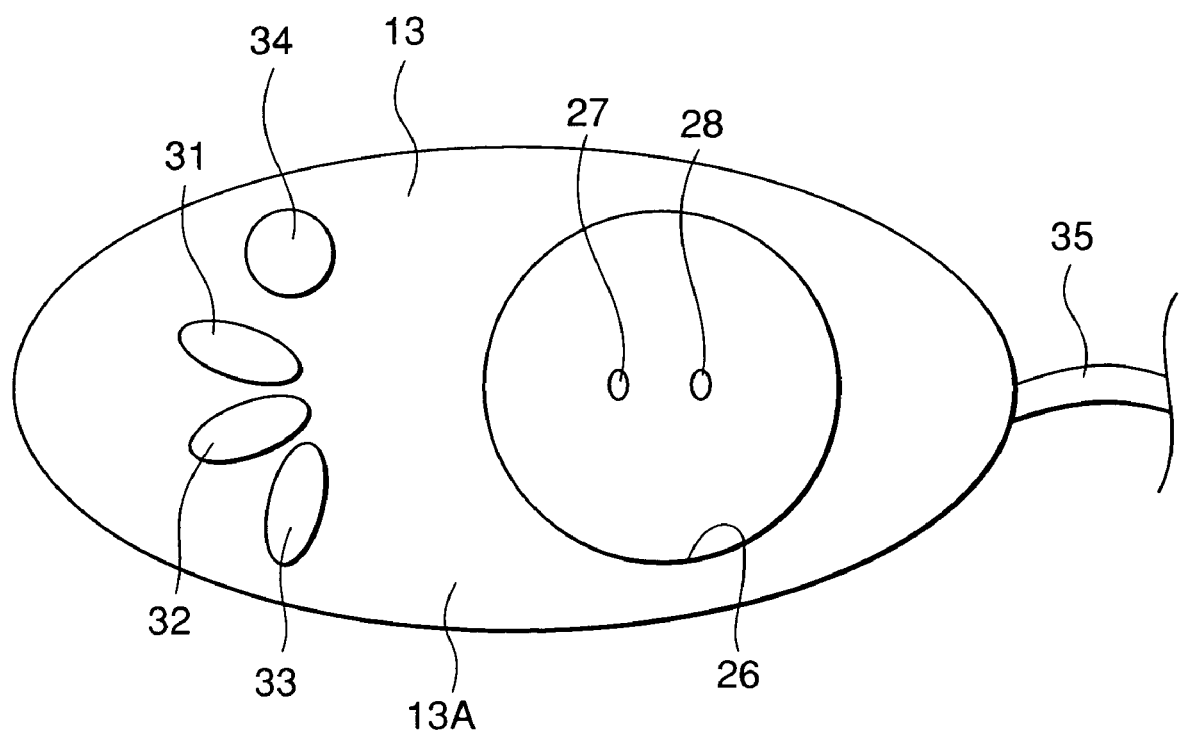
FIG. 7 is a plan view of a power supply of the electrolyzed water producing device.

Next, the aforementioned power supply 13 will be described with reference to FIG. 7. FIG. 7 is a plan view of the power supply 13. The power supply 13 is a direct current supply unit which supplies a direct current to the electrodes 5 and 6 in the applicator 12 and comprises a main body 13A which incorporates a microcomputer 25 as a controller and an AC/DC converter 30 which is capable of outputting a DC voltage of not lower than 100 V.

On the top surface of the main body 13A, a concave portion 26 for disposing the applicator 12 is formed. The concave portion 26 has a slightly larger size than that of the bottom of the applicator 12. In the concave portion 26, upwardly protruding terminals 27 and 28 are disposed, for example, in its central portion so as to make direct contact with the terminals 23 and 24 disposed at the bottom of the applicator 12.

Further, on the top surface of the main body 13A, three operation switches for controlling supply of power to the electrodes 5 and 6 of the applicator 12 disposed in the concave portion 26, in other words, turning on and off the power supply for the electrodes 5 and 6 are provided in the present embodiment. These operation switches are a "HIGH" switch 31, a "MEDIUM" switch 32, and a "LOW" switch 33. When any one of the switches 31, 32 and 33 is pressed, power is supplied to the electrodes 5 and 6, and when the switch pressed the last time among the switches 31, 32 and 33 is pressed again, supply of the power to the electrodes 5 and 6 is stopped.

To be more specific, three different ranks of voltage values are allocated to the operation switches 31, 32 and 33. At the press of the "HIGH" switch 31, the highest voltage value such as a DC voltage of 100 V is applied to the electrodes 5 and 6. Further, at the press of the "MEDIUM" switch 32, a voltage value lower than the voltage value allocated to the "HIGH" switch 31 is applied to the electrodes 5 and 6. In addition, at the press of the "LOW" switch 33, a voltage value lower than the voltage value allocated to the "MEDIUM" switch 32 is applied to the electrodes 5 and 6.

Further, an LED 34 formed on the top surface of the main body 13 is used for informing completion of electrolysis. In addition, on the side of the main body 13A, a cord 35 for supplying AC power is provided.

Figure 8:
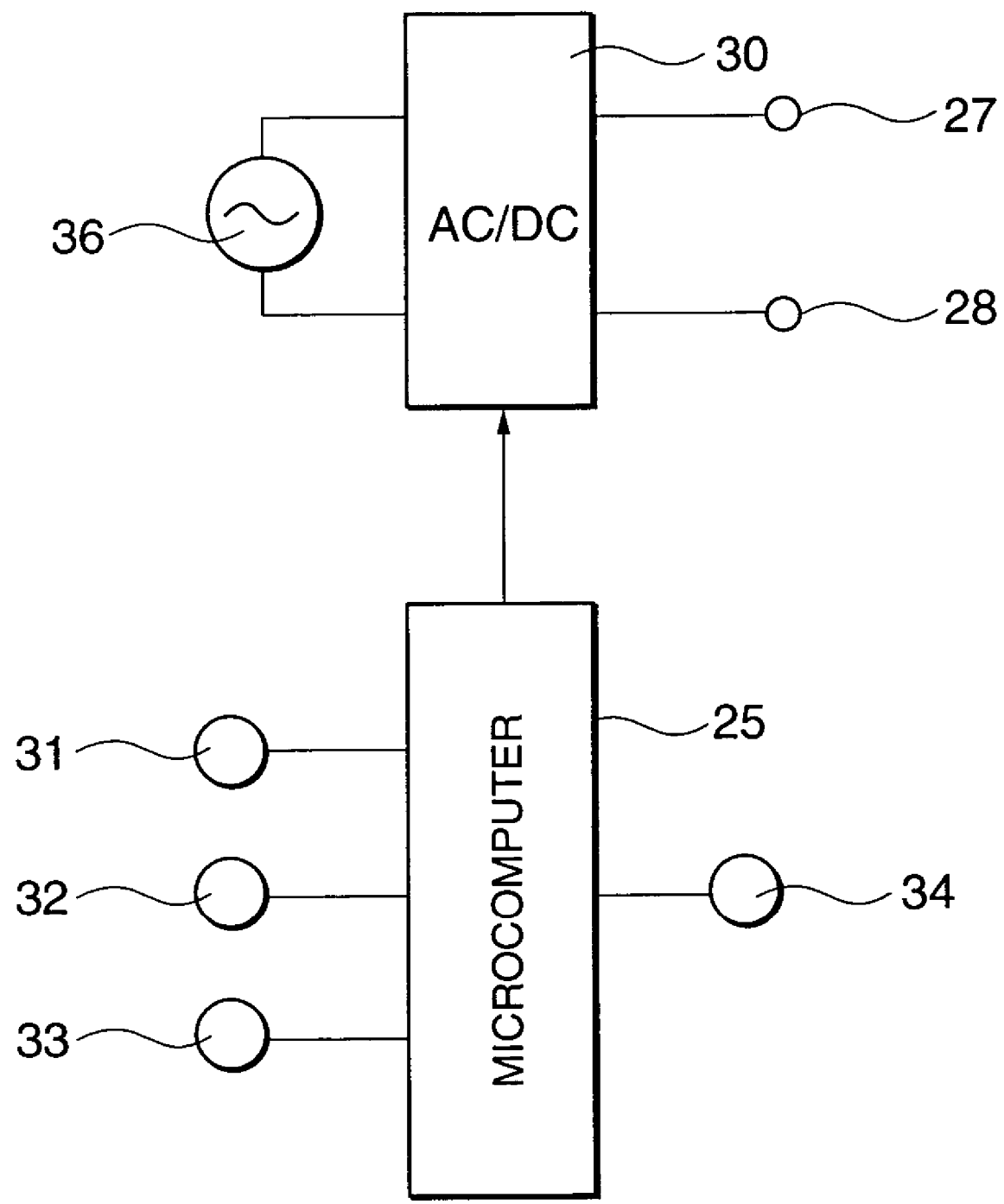
FIG. 8 is a block diagram showing a microcomputer and an AC/DC converter in the electrolyzed water producing device.

Next, with reference to FIG. 8 which is a block diagram showing the microcomputer 25 and the AC/DC converter 30, the microcomputer 25 and the AC/DC converter 30 will be described. The microcomputer 25 in the main body 13A has time means. To the input side of the microcomputer 25, the above operation switches 31, 32 and 33 are connected, while to the output side of the microcomputer 25, the LED 34 is connected. Further, the microcomputer 25 is connected to the above AC/DC converter 30.

To the input side of the AC/DC converter 30, an AC power supply 36 is connected, while to the output side of the AC/DC converter 30, the terminals 27 and 28 provided in the concave portion 26 of the main body 13A. The microcomputer 25 is-provided with power from the AC/DC converter 30 and controls various units.

Next, an application of the electrolyzed water producing device 10 will be described. Firstly, the cap 17A of the applicator 12 is removed so as to charge service water as for-electrolysis water into the reservoir 14. In the service water in the present embodiment, about 30 ppm of chloride ions are contained as an example of halogen ions or compounds containing halogen ions. Then, the opening of the reservoir 14 is closed again with the cap 17A of the applicator 12, and the applicator 12 is then set in the concave portion 26 of the power supply 13.

Then, at the press of any one of the operation switches 31, 32 and 33, the microcomputer 25 supplies a current of the voltage value corresponding to the pressed operation switch to the terminals 27 and 28 via the AC/DC converter 30. The terminals 27 and 28 supply power to the electrodes 5 and 6 via the terminals 23 and 24 provided at the bottom of the applicator 12. In the present embodiment, one of the electrodes 5 and 6 to which (+) is applied acts as an anode, and the other of the electrodes 5 and 6 to which (−) is applied acts as a cathode.

Then, due to the presence of the chloride ions in the service water as for-electrolysis water, at the electrode 5 or 6 which acts as an anode, the tantalum oxide existing in the electrode catalyst surface layer acts as a catalyst in electrolysis as described above, thereby suppressing production of oxygen and invigorating production of ozone. As a result, neutral electrolyzed water (sterilized water) containing a high concentration of ozone or active oxygen is produced in the reservoir 14.

Further, in the present embodiment as well, since the above electrode catalyst surface layer contains the tantalum oxide as a dielectric in an amount of more than 70 mol %, catalytic action in electrolysis is invigorated, production of oxygen is suppressed, and the efficiency of production of ozone can be further improved.

FIG. 9 shows the results of examining relationships between densities of electrode currents and concentrations of produced ozone by experiment when the tantalum-based electrode for electrolysis and a platinum-based electrode for electrolysis (comprising only a platinum oxide) are used. As is obvious from FIG. 9, with the tantalum (Ta) based electrode of the present embodiment, ozone is produced more vigorously and ozone concentration is higher than with the platinum (Pt) based electrode. Accordingly, required ozone concentration can be obtained at a lower current density (in this case, an electrode area subjected to the experiment is 8 $cm^2$, the amount of for-electrolysis water is 300 $cm^3$, and electrolysis time is 3 minutes).

Further, at the electrodes 5 and 6 having the electrode catalyst surface layer, superoxide ions and hydroxyl radicals (active oxygen) can also be produced as described above. Thus, due to produced ozone, superoxide ions and hydroxyl radicals, electrolyzed water exerts a high sterilizing effect on microorganisms such as bacteria, fungi and protozoans.

Further, since a portion of the electrode catalyst surface layer which is not constituted by the tantalum oxide is constituted by a noble metal or metal oxide such as platinum, the conductivity of the electrode 5 or 6 is improved by the platinum or the like, whereby the efficiency of electrolysis is improved.

Further, in the present embodiment as well, a mixture of a tantalum oxide and a noble metal or metal oxide is used as the surface layer forming material to be applied on the surface of the conductive substrate. However, the same effect as described above can still be achieved with such a mixture of a tantalum oxide precursor and a noble metal or metal oxide as described above.

Further, in the present embodiment as well, the electrodes 5 and 6 are constituted by the surface layer forming material comprising more than 70 mol % of dielectric, i.e., 90 mol % of tantalum oxide, and 10 mol % of platinum as a noble metal or metal oxide. In addition to this, the electrode may also be constituted such that the tantalum oxide constitutes more than 70% of the surface area of the electrode catalyst portion of the electrode after the electrode catalyst surface layer is formed by the surface layer forming material, that is, the portion which is immersed in for-treatment water so as to directly contribute to electrolysis.

Further, in the electrode catalyst portions of the electrodes 5 and 6, a noble metal or a metal oxide exists in surface portions of the electrode catalysts which are not constituted by the tantalum oxide which is a dielectric. This can also invigorate the catalytic actions of the electrodes 5 and 6 and improve the conductivities of the electrodes 5 and 6, whereby the efficiency of production of ozone can be improved.

Furthermore, in the present embodiment as well, the conductive substrate of the electrode comprises platinum. Alternatively, as in the foregoing case, the conductive substrate may comprise tantalum or a tantalum alloy and be oxidized to form the electrode catalyst surface layer.

In addition, since electrodes which are liable to be eluted are not used as the electrodes 5 and 6 in the present embodiment, replacement of electrodes due to elution is not required, so that ease of maintenance is improved. Further, oxygen and hydrogen produced by electrolysis of the service water as for-electrolysis water are discharged out of the reservoir 14 through the foregoing vent hole or pressure value preformed in the cap 17A of the discharge portion 17.

The microcomputer 25 monitors time lapsed since any one of the operation switches 31, 32 and 33 has been pressed down by the time means. After passage of a predetermined amount of time, e.g., about 1 minute to several minutes in the present embodiment, the microprocessor 25 determines that electrolyzed water containing ozone and active oxygen has been produced from for-electrolysis water in the applicator 12, stops supplying power to the electrodes 5 and 6, and terminates electrolysis. At this point, to notify a user of the termination of the electrolysis, the microcomputer 25 lights the LED 34.

Each time any one of the operation switches 31, 32 and 33 is pressed to carry out electrolysis, the microcomputer 25 controls the AC/DC converter 30 to switch polarities of the terminals 27 and 28.

Thereby, adhesion of substances such as chlorine which are produced at the electrode 5 or 6 which serves as a cathode by electrolysis is prevented, so that a reduction in electrolysis efficiency due to a reduction in efficiency of energization of the electrodes 5 and 6 can be prevented from occurring.

Then, by operation of the operating part 21 of the applicator 12, the thus produced electrolyzed water is sprayed against objects or sites to be sterilized such as hands and fingers, a bathroom, a kitchen and foliage plants so as to sterilize them.

In this case, since the applicator 12 itself in which the electrolyzed water has been produced can be carried around, the electrolyzed water can be used immediately after produced, and sterilization can be carried out with the electrolyzed water containing high concentrations of ozone and active oxygen which are readily decomposed and having a high sterilizing effect. Thereby, even spores which have been difficult to kill by a sterilization process using an agent can be killed. Further, since sterilization with the above electrolyzed water does not involve no agents, no problems which are hazardous to the environment are incurred.

Particularly, since not hypochlorous acid but ozone and active oxygen are produced in the for-electrolysis water to be used for sterilization, no salts remain on hands and fingers after application of the water, so that an inconvenience of having to rinse the hands and fingers after its application can also be eliminated.

Further, when the electrolyzed water is mixed with an acidic agent, production of a toxic chlorine gas can be prevented. In addition, since the electrolyzed water is obtained through electrolysis of service water, the electrolyzed water, unlike agents, causes no problems which are hazardous to the environment.

When electrolyzed water produced after passage of a predetermined amount of time, e.g., about 1 minute, from press of any one of the operation switches 31, 32 and 33 of the power supply 13 is used, energy loss does not occur as compared with when electrolysis is carried out constantly, and the freshly produced electrolyzed water having a significantly high sterilizing effect can be used for sterilization.

As described above, in the present invention, the concentration of electrolyzed water produced in the reservoir 14 can be changed by operation of the operation switches 31, 32 and 33. Accordingly, the concentrations of ozone and active oxygen can be adjusted according to application purpose of the electrolyzed water. In addition to adjustment of the concentrations of ozone and active oxygen by means of different voltages allocated to the operation switches 31, 32 and 33, the concentrations of ozone and active oxygen may also be adjusted by control of electrolysis time.

Further, it is known that ozone is not produced when, for example, pure water is used as for-electrolysis water in place of service water. In that case, it is appropriate to add chlorine (halogen or a compound containing halide ions). However, when the concentration of chloride ions (halide ions) becomes too high, production of hypochlorous acid (hypohalogenous acid) is invigorated, and production of ozone is suppressed. Therefore, chlorine should be added in a small amount so that the concentration of chloride ions in the pure water is close to that of the service water.

Further, in the electrolyzed water producing device 10 of the present invention, the above electrolyzed water is produced from for-electrolysis water in the portable applicator 12. Therefore, immediately after production of the electrolyzed water, a user can easily spray the electrolyzed water produced in the reservoir 14 against sites needed to be sterilized with the applicator 12 in hand. Thus, the sprayed sites can be sterilized easily.

Thus, the electrolyzed water can be carried and sprayed anywhere, thereby improving usability. Accordingly, hands, fingers, a bathroom or a kitchen can be sterilized easily and kept sanitary. Further, since the electrolyzed water can be used immediately after produced from the for-electrolysis water, bactericidal activity is improved.

As described above, ozone and active oxygen produced by electrolysis are not liable to remain and disappear upon replacement of containers. However, according to the present invention, since the electrolyzed water can be sprayed directly from the applicator 12 containing produced ozone and active oxygen, sterilization can be carried out without losing sterilizing effects of ozone and active oxygen.

Further, the power supply 13 for energizing the electrodes 5 and 6 of the applicator 12 from outside the applicator 12 is provided independently of the applicator 12. Since the power supply 13 which outputs a high voltage for production of ozone is not provided in the applicator 12, the weight of the applicator 12 can be reduced, and its structure can also be simplified. In addition, since the applicator 12 itself is light, the usability can be further improved.

Further, since the microcomputer 25 as a controller is provided in the power supply 13, the weight of the applicator 12 can be further reduced, and its structure can be further simplified.

Furthermore, although the electrolyzed water producing device 10 of the present embodiment has the power supply 13 independently of the applicator 12, it may also be an electrolyzed water producing device in which the power supply for energizing the electrodes 5 and 6 provided in the applicator 12 is integrated with the applicator 12. In this case, the power supply may be any of a secondary battery, a battery, a DC power supply and an AC power supply.

In that case, since the applicator 12 is integrated with the power supply, the device 10 does not need to have such a structure that the terminals of the power supply are in contact with the terminals of the electrodes 5 and 6. Thus, the structure of the device 10 is simplified, so that occurrences of failures can be inhibited.

Further, since the applicator 12 is a so-called spray-type applicator, it can push the electrolyzed water produced in the reservoir 14 to the discharge portion 17 and spray the electrolyzed water from the outlet 19 based on operation of the operating part 21. Thus, the operability of the applicator 12 can be improved. Further, since the applicator 12 is capable of discharging the electrolyzed water not in the form of fine sprays, it can be prevented from occurring that an operator inhales the electrolyzed water directly.

Although the tantalum-based electrodes are used in the present embodiment, titanium (or a titanium alloy) coated with an alloy of platinum and iridium may be used as an electrode material. However, it is needless to say that although the efficiency of production of ozone in that case becomes lower than that in the present embodiment as described-above, it is still effective depending on application forms.

As described in detail above, according to the present invention, an electrode of the present invention is an electrode for electrolysis which has an electrode catalyst at least on the surface and produces ozone or active oxygen in for-treatment water by electrolysis, wherein the electrode catalyst contains a dielectric, which occupies more than 70% of the surface area of the electrode catalyst. The dielectric constituting the electrode catalyst invigorates catalytic action in electrolysis, suppresses production of oxygen, more significantly contributes to production of ozone or active oxygen, and can improve the efficiency of production of ozone or active oxygen accordingly.

Further, a noble metal or metal oxide is present in a surface portion of the electrode catalyst which is not constituted by the dielectric. Hence, the catalytic action of the electrode is invigorated, and the conductivity of the electrode is improved, whereby the efficiency of production of ozone can be improved.

Further, an electrode of the present invention is an electrode for electrolysis which has an electrode catalyst surface layer formed on the surface of a conductive substrate and produces ozone or active oxygen in for-treatment water by electrolysis, wherein the electrode catalyst surface layer contains a dielectric in an amount of more than 70 mol %. The dielectric constituting the electrode catalyst surface layer invigorates catalytic action in electrolysis, suppresses production of oxygen, significantly contributes to production of ozone or active oxygen, and can increase the amount of production of ozone or active oxygen accordingly.

Further, the electrode catalyst surface layer contains a noble metal or metal oxide. Thereby, the conductivity of the electrode is improved, so that electrolysis efficiency can be improved.

Further, the electrode catalyst surface layer contains at least a tantalum oxide in an amount of 70 mol % as the dielectric and contains at least platinum as the noble metal or metal oxide, or the electrode catalyst surface layer contains at least a niobium oxide in an amount of 70 mol % as the dielectric and contains at least a ruthenium oxide as the noble metal or metal oxide. Thereby, catalytic action in electrolysis is invigorated, production of oxygen is suppressed, and the efficiency of production of ozone or active oxygen can be further improved accordingly.

Further, the electrode for electrolysis is produced by coating the surface of the conductive substrate with a surface layer forming material containing a tantalum oxide, a tantalum oxide precursor, a niobium oxide or a niobium oxide precursor, and heat-treating the conductive substrate and the surface layer forming material in an oxidizing atmosphere. Thereby, adhesion between the surface layer forming material and the conductive substrate is improved, and a dense electrode catalyst surface layer can be formed.

Further, the surface of the electrode contains the tantalum oxide or niobium oxide in an amount of more than 70 mol %. The tantalum oxide or niobium oxide suppresses production of oxygen, significantly contributes to production of ozone or active oxygen, and can increase the amount of production of ozone or active oxygen.

Further, if the electrode for electrolysis is produced by oxidizing the conductive substrate which is tantalum, a tantalum alloy, niobium or a niobium alloy so as to form the electrode catalyst surface layer, the electrode for electrolysis can be formed without using relatively expensive noble metals, and costs can be reduced accordingly.

Further, an anode and a cathode are immersed in for-treatment water in an electrolysis vessel, and the electrode for electrolysis is used as the anode. Therefore, active oxygen radicals and hydroxy radicals can also be produced.

Further, since the anode and the cathode are separated from each other by a cation exchange membrane, the amount of production of ozone can be increased by moving cations present on the anode side, i.e., hydrogen ions produced mainly at the time of production of ozone to the cation side by means of the cation exchange membrane.

Further, an anode and a cathode are immersed in for-treatment water in an electrolysis vessel, the electrode for electrolysis is used as the anode and the cathode, and a pulse voltage is applied to between the anode and the cathode in the for-treatment water. Consequently, hydroxy radicals can be produced effectively.

Further, an electrolyzed water producing device of the present invention has a portable applicator comprising a reservoir for reserving water to be electrolyzed, a pair or plurality of electrodes for electrolysis which are provided in the reservoir so as to be immersed in the for-electrolysis water, and an outlet for discharging the liquid out of the reservoir, and passes an electric current in between the electrodes so as to produce ozone or active oxygen in the for-electrolysis water. Accordingly, with the applicator in hand, a user can easily apply electrolyzed water produced in the reservoir to sites needed to be sterilized. Thus, the applied sites can be sterilized easily.

Hence, the usability of the electrolyzed water is improved. Further, the electrolyzed water can be used immediately after produced, and sterilization can be carried out by use of the electrolyzed water containing a high concentration of ozone or active oxygen and having a high sterilizing effect. Thereby, even spores which have been difficult to kill by a sterilization process using an agent can be killed. Further, since sterilization with the above electrolyzed water does not involve no agents, no problems which are hazardous to the environment are incurred.

Particularly, since not hypochlorous acid but ozone or active oxygen is produced in the for-electrolysis water to be used for sterilization, no salts remain after application of the water, and an inconvenience of having to rinse again can be eliminated accordingly.

Further, according to the electrolyzed water producing device of the present invention, the electrode has an electrode catalyst at least on the surface, the electrode catalyst contains a dielectric, and the dielectric constitutes more than 70% of the surface area of the electrode catalyst. The dielectric constituting the electrode catalyst invigorates catalytic action in electrolysis, suppresses production of oxygen, more significantly contributes to production of ozone or active oxygen, and can improve the efficiency of production of ozone or active oxygen accordingly.

Further, according to the electrolyzed water producing device of the present invention, a noble metal or metal oxide is present in a surface portion of the electrode catalyst which is not constituted by the dielectric. Hence, the catalytic action of the electrode can be invigorated, and the conductivity of the electrode can be improved, whereby the efficiency of production of ozone can be improved.

Further, according to the electrolyzed water producing device of the present invention, the electrode has an electrode catalyst surface layer formed on the surface of a conductive substrate, and the electrode catalyst surface layer contains a dielectric in an amount of more than 70 mol %. The dielectric constituting the electrode catalyst surface layer invigorates catalytic action in electrolysis, suppresses production of oxygen, significantly contributes to production of ozone or active oxygen, and can increase the amount of production of ozone or active oxygen accordingly.

Further, according to the electrolyzed water producing device of the present invention, the electrode catalyst surface layer contains at least a tantalum oxide in an amount of 70 mol % as the dielectric and contains at least platinum as the noble metal or metal oxide, or the electrode catalyst surface layer contains at least a niobium oxide in an amount of 70 mol % as the dielectric and contains at least a ruthenium oxide as the noble metal or metal oxide. Thereby, catalytic action in electrolysis is invigorated, production of oxygen is suppressed, and the efficiency of production of ozone or active oxygen can be further improved accordingly.

Further, according to the electrolyzed water producing device of the present invention, the electrode comprises titanium coated with a mixture of platinum as the noble metal or metal oxide and a tantalum oxide. The tantalum oxide as a dielectric acts as a catalyst, suppresses production of oxygen, significantly contributes to production of ozone or active oxygen, and can improve the efficiency of production of ozone or active oxygen accordingly.

Further, according to the electrolyzed water producing device of the present invention, since a power supply for energizing the electrodes in the applicator from outside the applicator is provided independently of the applicator, the applicator itself can be made lightweight, and its structure can also be simplified. Further, since the applicator itself is lightweight, usability can be further improved.

Further, according to the electrolyzed water producing device of the present invention, since the applicator incorporates a power supply for energizing the electrodes, the structure of the device is simplified, so that occurrences of failures can be inhibited.

Further, according to the electrolyzed water producing device of the present invention, a controller for controlling energization of the electrodes is provided, and the controller is capable of changing the concentration of electrolyzed water produced in the reservoir. Accordingly, the concentration of ozone or active oxygen can be adjusted according to application purpose of the electrolyzed water.

Further, according to the electrolyzed water producing device of the present invention, since the controller is provided in the power supply, the weight of the applicator can be further reduced, and its structure can also be further simplified.

Further, according to the electrolyzed water producing device of the present invention, since the controller switches polarities of the electrodes from one polarity to the other polarity, adhesion of substances such as chlorine which are produced at the electrode which serves as a cathode by electrolysis is prevented, and a reduction in electrolysis efficiency due to a reduction in efficiency of energization of the electrodes can be prevented from occurring accordingly.

Further, according to the electrolyzed water producing device of the present invention, the applicator has an operating part, and based on operation of the operating part, the electrolyzed water produced in the reservoir is pushed toward the outlet so as to be sprayed out therefrom. Hence, the operability of the applicator can be improved.

What is claimed is:

1. An electrode for electrolysis which has an electrode catalyst at least on the surface and produces ozone or active oxygen in for-treatment water by electrolysis, wherein
the electrode catalyst contains a dielectric, which occupies more than 70% of the surface area of the electrode catalyst.

2. The electrode of claim 1, wherein a noble metal or metal oxide is present in a surface portion of the electrode catalyst which is not constituted by the dielectric.

3. An electrolytic process for producing ozone or active oxygen, wherein an anode and a cathode are immersed in for-treatment water in an electrolysis vessel, and the electrode of claim 1, is used as the anode.

4. The process of claim 3, wherein the anode and the cathode are separated from each other by a cation exchange membrane.

5. An electrolytic process for producing ozone or active oxygen, wherein an anode and a cathode are immersed in for-treatment water in an electrolysis vessel, the electrode of claim 1 is used as the anode and the cathode, and a pulse voltage is applied to between the anode and the cathode in the for-treatment water.

6. An electrode for electrolysis which has an electrode catalyst surface formed on the surface of a conductive substrate and produces ozone or active oxygen in for-treatment water by electrolysis, wherein
the electrode catalyst surface layer contains a dielectric in an amount of more than 70 mol%.

7. The electrode of claim 6, wherein the electrode catalyst surface layer contains a noble metal or metal oxide.

8. The electrode of claim 7, wherein the electrode catalyst surface layer contains at least a tantalum oxide in an amount of 70 mol% as the dielectric and contains at least platinum as the noble metal or metal oxide, or the electrode catalyst surface layer contains at least a niobium oxide in an amount of 70 mol% as the dielectric and contains at least a ruthenium oxide as the noble metal or metal oxide.

9. A process for producing the electrode of claim 6, comprising the steps of:
coating the surface of the conductive substrate with a surface layer forming material containing a tantalum oxide, a tantalum oxide precursor, a niobium oxide or a niobium oxide precursor, and
heat-treating the conductive substrate and the surface layer forming material in an oxidizing atmosphere.

10. A process for producing the electrode of claim 6, wherein the conductive substrate which is tantalum, a tantalum alloy, niobium or a niobium alloy is oxidized to form the electrode catalyst surface layer.

11. An electrolyzed water producing device,
which has a portable applicator comprising:
a reservoir for reserving water to be electrolyzed,
a pair or plurality of electrodes for electrolysis which are provided in the reservoir so as to be immersed in the for-electrolysis water, and
an outlet for discharging the liquid out of the reservoir, and
which passes an electric current in between the electrodes so as to produce ozone or active oxygen in the for-electrolysis water,
wherein the electrode has an electrode catalyst at least on the surface, the electrode catalyst contains a dielectric, and the dielectric constitutes more than 70% of the surface area of the electrode catalyst.

12. The device of claim 11, wherein a noble metal oxide is present in a surface portion of the electrode catalyst which is not constituted by the dielectric.

13. An electrolyzed water producing device,
which has a portable applicator comprising:
a reservoir for reserving water to be electrolyzed,
a pair or plurality of electrodes for electrolysis which are provided in the reservoir so as to be immersed in the for-electrolysis water, and
an outlet for discharging the liquid out of the reservoir, and
which passes an electric current in between the electrodes so as to produce ozone or active oxygen in the for-electrolysis water.
wherein the electrode has an electrode catalyst surface layer formed on the surface of a conductive substrate, and the electrode catalyst surface layer contains a dielectric in an amount of more than 70 mol%.

14. The device of claim 13, wherein the electrode catalyst surface layer contains at least a tantalum oxide in an amount of 70 mol% as the dielectric and contains at least platinum as the noble metal or metal oxide, or the electrode catalyst surface layer contains at least a niobium oxide in an amount of 70 mol% as the dielectric and contains at least ruthenium oxide as the noble metal or metal oxide.

15. An electrolyzed water producing device,
which has a portable applicator comprising:
a reservoir for reserving water to be electrolyzed,
a pair or plurality of electrodes for electrolysis which are provided in the reservoir so as to be immersed in the for-electrolysis water, and
an outlet for discharging the liquid out of the reservoir, and
which passes an electric current in between the electrodes so as to produce ozone or active oxygen in the for-electrolysis water,
wherein the electrode comprises titanium coated with a mixture of platinum as the noble metal or metal oxide and a tantalum oxide as the dielectric.

16. An electrolyzed water producing device, comprising:
a portable applicator, said portable applicator comprising:
a reservoir for reserving water to be electrolyzed,
a pair or plurality of electrodes for electrolysis which are provided in the reservoir so as to be immersed in the for-electrolysis water,
terminals, connected to said electrodes, at the exterior of the reservoir, and
an outlet for discharging the liquid out of the reservoir, and
which passes an electric current in between the electrodes so as to produce ozone or active oxygen in the for-electrolysis water;
a power supply, independent of the applicator, for energizing the electrodes in the applicator from outside the applicator; and
terminals connected to said power supply for making contact with the terminals connected to the electrodes.

17. The device of claim 16, wherein a controller for controlling the value of the voltage applied to the electrodes is provided, and the controller is capable of changing the concentration of electrolyzed water produced in the reservoir.

18. The device of claim 17, wherein the controller is provided in the power supply.

19. The device of claim 17, wherein the controller switches polarities of the electrodes from one polarity to the other polarity.

20. The device of claim 17, wherein the applicator has an operating part, and based on operation of the operating part, the electrolyzed water produced in the reservoir is pushed toward the outlet so as to be sprayed out therefrom.

21. The device of claim 16, wherein the applicator has an operating part, and based on operation of the operating part, the electrolyzed water produced in the reservoir is pushed toward the outlet so as to be sprayed out therefrom.

* * * * *